US009066787B1

(12) United States Patent
Price et al.

(10) Patent No.: US 9,066,787 B1
(45) Date of Patent: Jun. 30, 2015

(54) LATERALLY APPLIED ORTHOSIS

(76) Inventors: Stephen A. Price, Tampa, FL (US); Mary P. Price, Tampa, FL (US)

(*) Notice: Subject to any disclaimer, the term of this patent is extended or adjusted under 35 U.S.C. 154(b) by 0 days.

(21) Appl. No.: 13/363,854

(22) Filed: Feb. 1, 2012

Related U.S. Application Data

(63) Continuation-in-part of application No. 12/559,111, filed on Sep. 14, 2009.

(51) Int. Cl.
*A61F 5/00* (2006.01)
*A63B 21/02* (2006.01)
*A61F 5/01* (2006.01)
*A63B 21/00* (2006.01)
*A63B 23/035* (2006.01)

(52) U.S. Cl.
CPC ............. *A61F 5/0102* (2013.01); *A61F 5/0104* (2013.01); *A61F 5/0106* (2013.01); *A61F 5/0118* (2013.01); *A63B 21/02* (2013.01); *A63B 21/1403* (2013.01); *A63B 21/1449* (2013.01); *A63B 23/035* (2013.01)

(58) Field of Classification Search
CPC ........... A61F 5/00; A61F 5/01; A61F 5/0102; A61F 5/0104; A61F 5/0106; A61F 5/0118; A63B 21/00; A63B 21/002; A63B 21/0023; A63B 21/02; A63B 21/055; A63B 21/0552; A63B 21/0555; A63B 21/14; A63B 21/1403; A63B 21/1423; A63B 21/1434; A63B 21/1446; A63B 21/1449; A63B 21/1484; A63B 23/00; A63B 23/035; A63B 23/03508; A63B 23/04; A63B 23/0494; A63B 23/12; A63B 23/1281

USPC .............. 602/6, 16, 20, 60–62; 128/878, 881, 128/882; 482/91, 105, 121, 122, 124, 148
See application file for complete search history.

(56) References Cited

U.S. PATENT DOCUMENTS

| | | | | |
|---|---|---|---|---|
| 3,703,171 | A * | 11/1972 | Schiavitto | 602/26 |
| 5,514,081 | A * | 5/1996 | Mann | 602/20 |
| 5,873,847 | A * | 2/1999 | Bennett et al. | 602/16 |
| 5,891,068 | A | 4/1999 | Kenney | |
| 5,921,945 | A * | 7/1999 | Gray | 602/5 |
| 6,001,074 | A | 12/1999 | Kenney | |
| 6,206,846 | B1 | 3/2001 | Kenney | |
| 6,261,253 | B1 | 7/2001 | Katzin | |
| 6,540,710 | B1 * | 4/2003 | Cruz | 602/21 |
| 6,656,097 | B2 * | 12/2003 | Karecki | 482/148 |
| 6,692,453 | B2 * | 2/2004 | Wolfe | 602/21 |
| 2007/0055191 | A1 * | 3/2007 | Farrell et al. | 602/21 |
| 2009/0320299 | A1 * | 12/2009 | Kuhn et al. | 30/169 |

* cited by examiner

*Primary Examiner* — Alireza Nia
*Assistant Examiner* — Keri J Nelson
(74) *Attorney, Agent, or Firm* — Dale J. Ream

(57) ABSTRACT

A laterally applied orthosis has a dynamic flexible stiffener that is configured to extend across a joint and to impede joint movement caused by muscle contractions by resisting flexing but allowing some movement in the joint. The stiffener is elastic so that it rebounds to its original form under its inherent bias after flexing due to movement of the joint. The stiffener is housed within a brace having a plurality of adjustable straps extending from the brace. The straps can be fastened to one another or the brace itself to form a substantially tubular structure for securing the brace to a limb. At least one of the plurality of straps is semi-rigid and malleable.

4 Claims, 7 Drawing Sheets

LATERALLY APPLIED ORTHOSIS

CROSS-REFERENCE TO RELATED APPLICATIONS

This application is a continuation-in-part of and claims priority to currently pending U.S. patent application Ser. No. 12/559,111, entitled "ORTHOSIS," filed on Sep. 14, 2009 by the same inventor, the contents of which are hereby incorporated by reference.

BACKGROUND OF THE INVENTION

1. Field of the Invention

This invention relates to an orthosis. More specifically, it relates to a laterally applied orthosis having a flexible stiffener.

2. Description of the Related Art

Patients who have suffered strokes, spinal cord injuries, muscular disorders or neurological disorders such as cerebral palsy and multiple sclerosis, often uncontrollably contract their joints in flexion, which can causes them to lose range of motion in their joints. The affected joints are the wrist, fingers, foot, toe, ankle joints, hip, elbow, and knee. In an attempt to treat or otherwise alleviate the potential loss of range of motion, physicians and physical therapists often secure an orthosis or splint across the affected joint to prevent uncontrollable flexion of the joint by stretching the joint to a desired position. The orthosis may be moved to a series of desired positions to stretch the joint and hopefully prevent a loss of range of motion.

Many different types of orthoses have been developed. For example, U.S. Pat. No. 6,261,253 to Katzin discloses a hand orthosis that limits finger and wrist flexion with a steel stiffener that provides a static resistance to the user. The stiffener is plastically deformed into the desired position to conform to the shape of the joint and surrounding limbs. However, the stiffener is made of material that resists forces to which it is normally subjected when worn by a patient. The patient is unable to move the stiffener during contracture because the stiffener provides a static resistance to the joint. While this property is useful in many circumstances, the needs of certain patients require a different type of stiffener.

Knee and elbow orthoses for treatment of undesirable flexural contractions of those joints are known. These knee and elbow orthoses use goniometers which are adjustable to allow a certain degree of joint movement. For example, where zero degrees represents the angle of a patient's arm or leg when it is straight, the goniometer can be adjusted so that the patient can only move his or her arm or leg a predetermined number of degrees freely within the range of movement allowed by the goniometer. For some patients it is undesirable to use an orthosis that allows this type of movement, even if it is only within a certain range.

Thus, while orthoses have been used to treat or alleviate the symptoms of uncontrollable joint flexion, there is a need for a laterally applied orthosis that resists flexing but which allows some joint movement.

SUMMARY OF THE INVENTION

The novel laterally applied orthosis has a dynamic, flexible stiffener made of spring steel that is configured to extend across a joint and impede joint movement caused by muscle contractions by resisting flexing but allowing some movement in the joint. The stiffener is elastic so that it rebounds to its original form after flexing due to movement of the joint.

The orthosis may be used to impede the movement of any joint. Preferably, however, the orthosis impedes movement of the wrist and finger joints, the elbow joint, the knee joint, the hip joint, or the ankle and toe joints by having the flexible stiffener extend across the affected joint. The elasticity or inherent bias of the stiffener allows joint movement but provides constant resistance to the movement until the joint returns to its position of repose.

For certain patients, the novel stiffener is better than conventional orthoses at preventing loss of range of motion due to its dynamic properties. The ability of the stiffener to provide a patient's joint with a range of motion, while resisting that joint motion, assists in preventing degeneration of the joint and the muscles connected to it. This feature is not present in conventional orthoses because a conventional orthosis allows no joint movement.

Moreover, the novel orthosis enables a health care provider to apply it laterally to a joint, regardless of joint contraction due to muscle flexion. Specifically, the dynamic, flexible stiffener that is housed within the orthosis is bent by the health care provider to correspond with the desired contraction angle of the joint. This is the position of repose of the orthosis and the inherent bias of the spring steel stiffener will urge the orthosis into this position of repose at all times. The health care provider then bends the orthosis as needed, overcoming the inherent bias of the spring steel but not exceeding its elastic limit, to position it on the joint by laterally sliding the flexed stiffener onto the contracted joint. The stiffener is then released so that it applies a constant force to the contracted joint.

In an elbow embodiment, the orthosis extends across a patient's elbow joint and includes a dynamic, flexible, elastic stiffener for impeding movement caused by muscle contraction. The stiffener includes a first configuration extending across the elbow joint of the patient when the patient's muscle is in repose and a second configuration extending across the elbow joint of the patient when the patient's muscle is under contraction. The stiffener allows some joint movement but resists flexion of the elbow joint to impede joint movement. The stiffener rebounds under its inherent bias from the second configuration to the first configuration after the contraction has terminated.

The stiffener is housed within a brace. The brace includes a medial side and a lateral side. When positioned on the patient, the brace extends from an upper arm to a forearm. The stiffener is disposed within the brace such that the stiffener extends from the medial side of the upper arm to the medial side of the forearm for impeding movement of the elbow joint.

A plurality of straps is secured to and extends from the brace. The straps may be fastened to one another or to the brace itself to form a substantially tubular structure for securing the brace to an arm. At least one strap of the plurality of straps is semi-rigid and malleable. The semi-rigid, malleable strap enables the brace to be positioned on the user from the side, thereby limiting the amount of movement required by the user to position the brace. Moreover, the semi-rigid, malleable strap is generally C-shaped, further limiting the amount of movement required by the user to position the brace.

Another embodiment of the novel orthosis impedes movement of a knee joint caused by muscle contraction. Like the elbow orthosis, the knee orthosis includes a stiffener, a brace, and a plurality of adjustable straps for securing the brace to a patient's leg. The brace is positioned on the posterior side of the patient's leg and is configured to retain the flexible dynamic stiffener. The stiffener extends from the posterior side of the upper leg to the posterior side of the lower leg for impeding movement of the knee joint.

The flexible dynamic stiffener for all of the embodiments is a heat treated and tempered spring steel. Unified Numbering System G10950 steel is preferred. Preferably, the stiffener includes steel having a yield tensile strength of between approximately 100 to 320 kilopounds per square inch, more preferably between approximately 150 to 275 kilopounds per square inch, even more preferably between approximately 200 to 250 kilopounds per square inch, and most preferably approximately 240 kilopounds per square inch.

The preferred steel has a modulus of elasticity of between approximately 150 to 300 GPa, more preferably between approximately 175 to 250 GPa, and most preferably between approximately 190 to 210 GPa. The stiffener preferably includes steel having a hardness on the Rockwell C scale of between approximately 45 to 60, more preferably between approximately 45 to 55, and most preferably between approximately 48 to 51.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The novel laterally applied orthosis includes a flexible dynamic stiffener having an inherent bias and a generally flat, rectangular shape. It is configured to have a longitudinal extent sufficient to extend across a joint and is elastic so that it rebounds to its original form after flexing due to joint movement caused by muscle contraction.

The novel orthosis can be configured to be used in conjunction with any articulating joint, but only two exemplary embodiments are disclosed herein. All other embodiments are obvious in view of the specifically disclosed embodiments. Thus, any type of orthosis having a flexible dynamic stiffener having an inherent bias as disclosed herein, including a hand/wrist, foot/ankle/toes, hip/knee, and hip/thigh orthosis, is within the scope of this invention.

Figure 1:
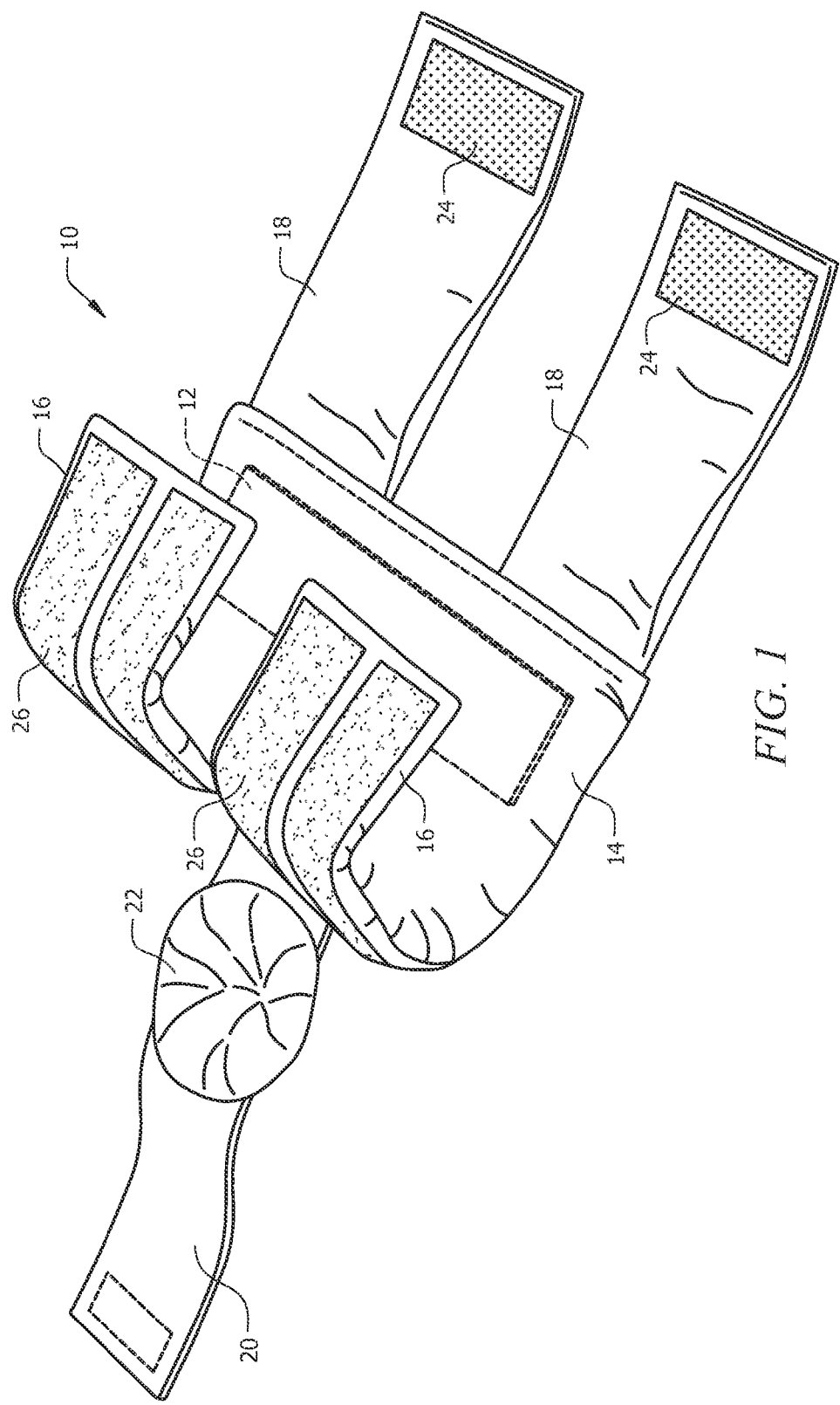
FIG. 1 is an upper perspective view of the orthosis in an open configuration.
Figure 2:
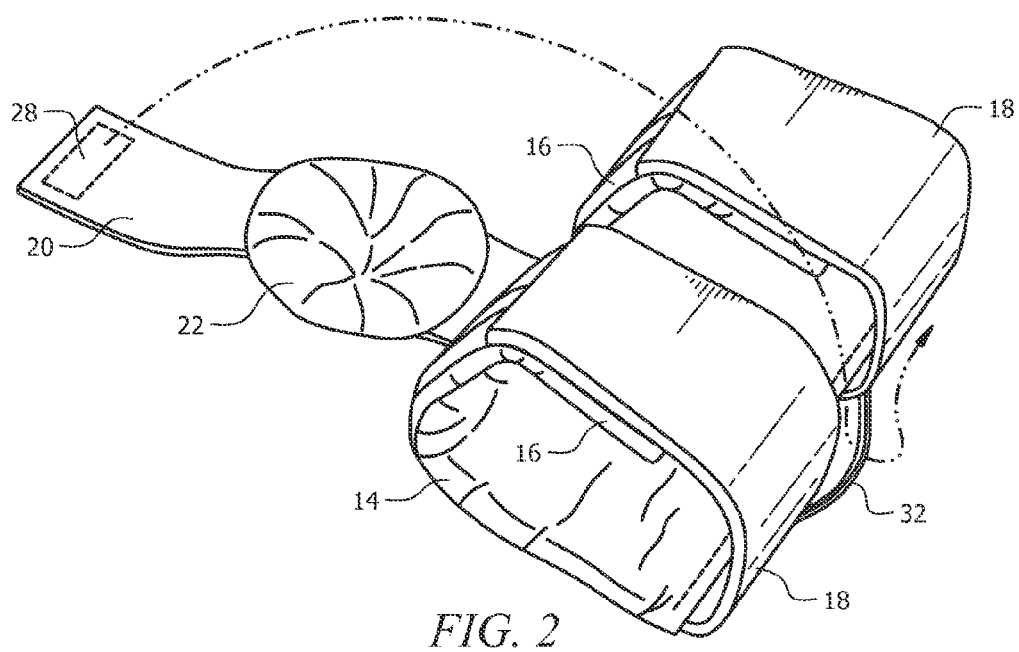
FIG. 2 is an upper perspective view of the orthosis in a partially closed configuration.
Figure 3:
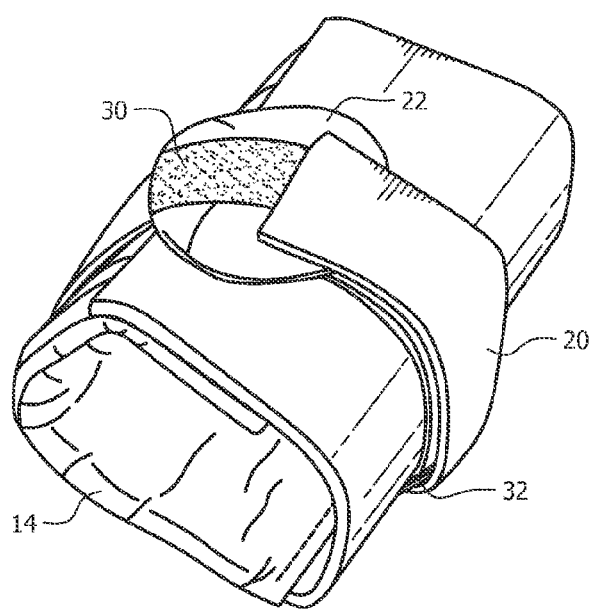
FIG. 3 is an upper perspective view of the orthosis in a closed configuration.

As depicted in FIGS. 1-3, the novel orthosis is generally denoted as 10 and includes flexible stiffener 12 housed within brace 14. Flexible stiffener 12 is of the same type described in detail for a knee and elbow orthosis in currently pending U.S. patent application Ser. No. 12/559,111, entitled "ORTHOSIS," filed on Sep. 14, 2009 by the same inventor, which is incorporated by reference into this disclosure as aforesaid.

Straps 18 extend transversely from brace 14 in parallel, spaced apart relation to one another as depicted in FIG. 1 and are releasably fastened, by hook and loop fastening means, to semi-rigid and malleable straps 16 or to brace 14 to form a substantially tubular structure for securing brace 14 to a knee or elbow. Semi-rigid, malleable straps 16 also extend transversely from brace 14 and are substantially C-shaped to facilitate the placement of brace 14 on a user from a lateral direction so that the limb to be treated need not be straightened in order to attach the novel orthosis thereto. In the claims that follow, straps 16 are referred as the first plurality of straps and straps 18 are referred to as the second plurality of straps.

Specifically, semi-rigid, malleable, C-shaped straps 16 enable orthosis 10 to be positioned on a patient from the side, i.e., laterally, without having to move or adjust the patient's arm or leg. The outer surface of semi-rigid and malleable straps 16 include fastener loops 26, and the distal ends of straps 18 include fastener hooks 24, or vice versa. Hooks 24 and loops 26 secure straps 18 and semi-rigid and malleable straps 16 together to form said substantially tubular structure.

Knee strap 20 extends transversely from brace 14 and includes knee pad 22. Knee strap 20 is wrapped around brace 14 to further form said substantially tubular structure and protects a knee or elbow of a user. The distal end of knee strap 20 includes hooks 28 as indicated in FIG. 2, and the outer surface of knee strap 20 includes loops 30, or vice versa. Knee strap 20 is folded over brace 14 and inserted through loop 32. Hooks 28 and loops 30 are then secured to one another.

Figure 4:
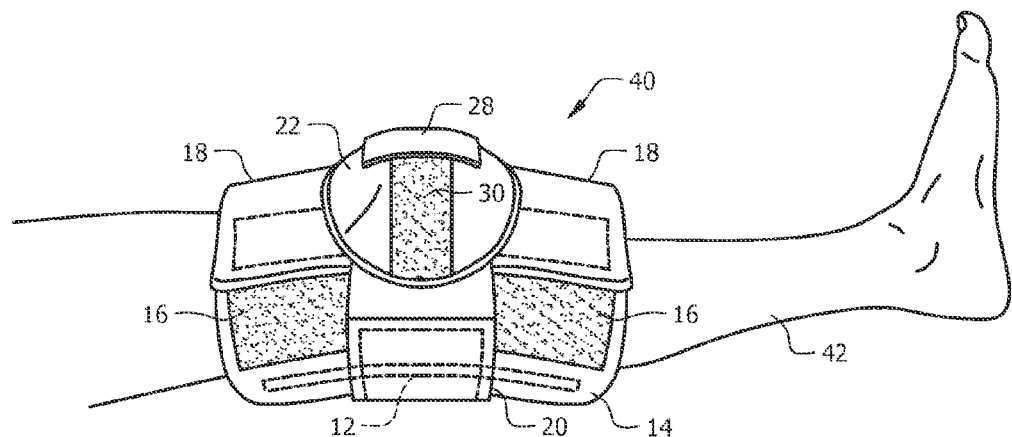
FIG. 4 is an upper perspective view of the orthosis positioned on a patient's extended leg.
Figure 5:
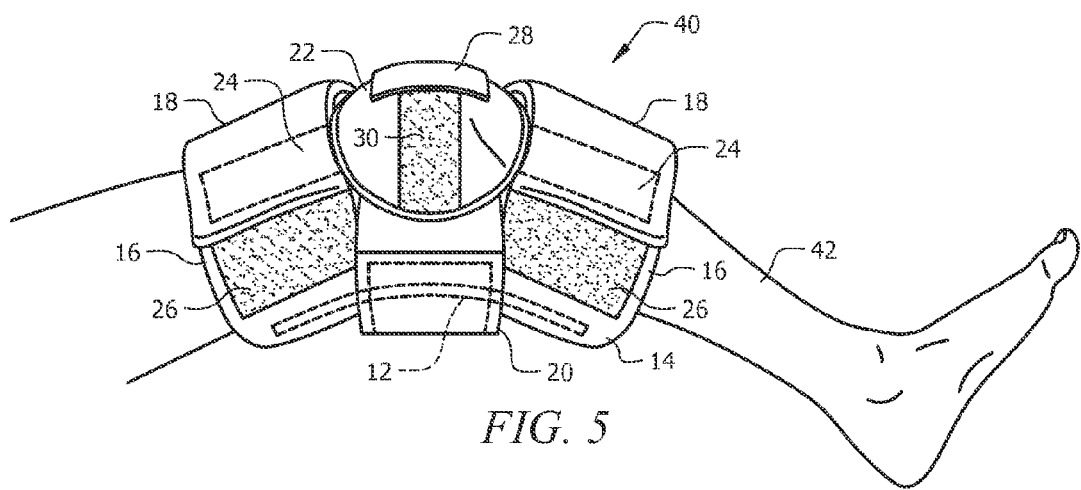
FIG. 5 is an upper perspective view of the orthosis positioned on a patient's partially contracted leg.
Figure 6:
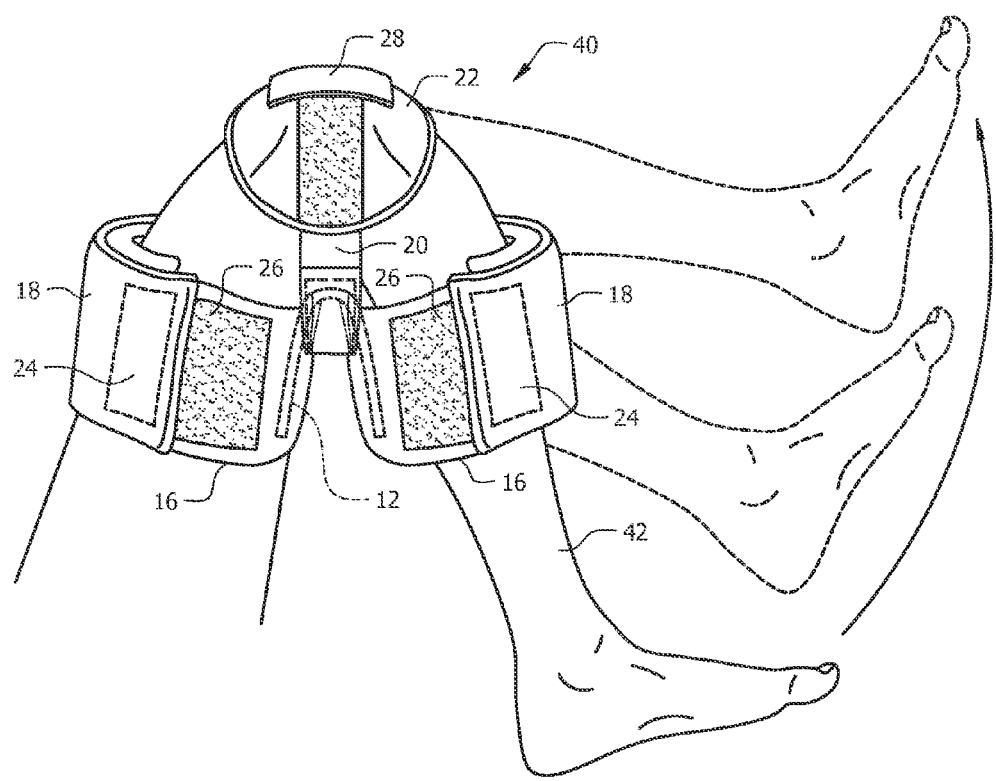
FIG. 6 is an upper perspective view of the orthosis positioned on a patient's fully contracted leg.

A knee orthosis is depicted generally as 40 in FIGS. 4-6. Knee orthosis 40 is substantially similar to an elbow orthosis except that knee orthosis 40 is slightly larger so that it can receive leg 42 and impede movement of a knee.

Knee orthosis 40 includes flexible stiffener 12 disposed within a pocket formed within brace 14. Straps 18 extend transversely from brace 14 as aforesaid and are adapted to be fastened to semi-rigid and malleable straps 16 or to brace 14 to form a substantially tubular structure for receiving leg 42. Semi-rigid, malleable straps 16 are substantially C-shaped and facilitate the placement of brace 14 on leg 42. The outer surface of semi-rigid and malleable straps 16 include loops 26, and the distal ends of straps 18 include hooks 24, or vice versa. Hooks 24 and loops 26 secure straps 18 and semi-rigid and malleable straps 16 together to form said substantially tubular structure.

Knee strap 20 extends from brace 14 and includes knee pad 22. Knee strap 20 is wrapped around brace 14 to further form said substantially tubular structure and protects the knee of leg 42. The distal end of knee strap 20 includes hooks 28, and the outer surface of knee strap 20 includes loops 30. Hooks 28 and loops 30 are secured together.

As depicted in FIG. 4, flexible stiffener 12 is in its position of repose when leg 42 is not contracted. As depicted in FIG. 5, however, flexible stiffener 12 is partially flexed as leg 42 is partially contracted. Likewise, as depicted in FIG. 6, flexible stiffener 12 is substantially fully flexed when leg 42 is substantially fully contracted. In both FIGS. 5 and 6, the inherent bias of flexible stiffener 12 provides a constant resistance to impede joint movement caused by muscle contractions. Once the muscle is no longer contracted, orthosis 40 returns to its position of repose as depicted in FIG. 4.

As depicted in FIG. 6, knee orthosis 40 enables a health care provider to apply it laterally to the joint, regardless of joint contraction due to flexion. Specifically, flexible stiffener 12 is initially bent by a qualified health care provider to correspond with a desired contraction angle of the joint. This initial bending defines the position of repose of the spring steel stiffener. Orthosis 40 is then flexed by the health care provider, momentarily overcoming the inherent bias of the spring steel, and positioned in operative relation to the joint by laterally sliding the flexed flexible stiffener 12 under the contracted joint. Flexible stiffener 12 is then released so that it returns to its position of repose under its inherent bias, thereby applying a constant force to the contracted joint. Once the stiffener resumes its position of repose, it resists flexion of the muscles causing the contraction, tiring the muscles and eventually straightening the joint. As a result, the joint will go from the configuration in FIG. 6 to FIG. 5 and eventually to FIG. 4.

Figure 7:
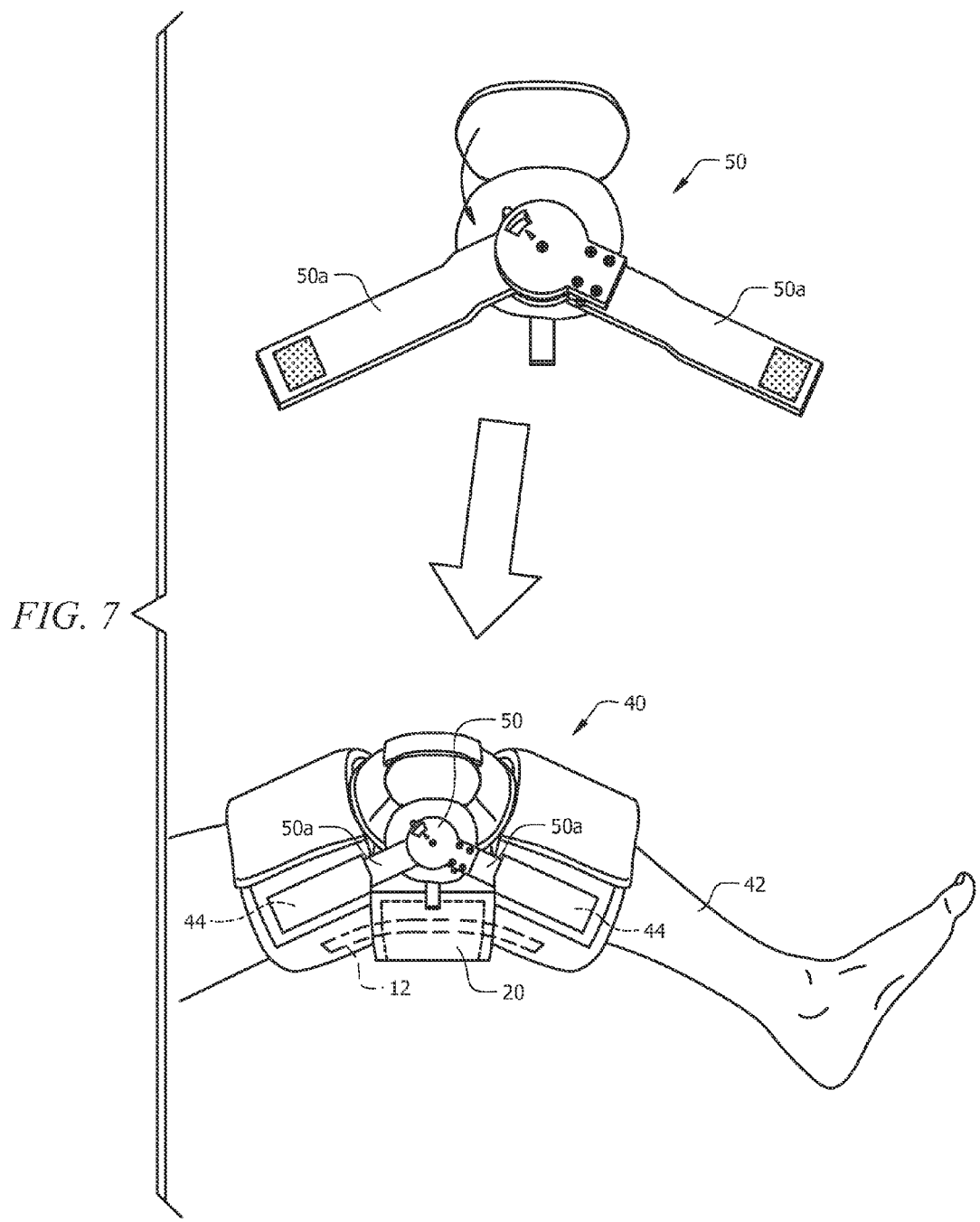
FIG. 7 is an upper perspective view of the orthosis including a goniometer.

FIG. 7 indicates that goniometer 50 may be attached to the lateral side of knee orthosis 40. Knee orthosis 40 may include pockets 44 disposed on the lateral side of brace 14 for receiving a corresponding end of goniometer 50. Pockets 44 are formed by flaps covered in hook and loop fastening material, i.e., two (2) flaps are sewn together about their respective peripheral edges to form a pocket between them. The flaps are not numbered in FIG. 7 but they are numbered in FIGS. 8A and 8B in connection with an elbow orthosis that has a structure similar to knee orthosis 40.

Conventional goniometer 50 includes rigid adjustable arms 50a, 50a to allow or prevent a certain degree of joint movement, said rigid arms extending radially from a central hub as depicted and being angularly adjustable with respect to said central hub.

Goniometer 50 works in conjunction with novel flexible stiffener 12 to prevent a user from completely contracting leg 42. For example, where one hundred eighty degrees (180°) represents the angle of a patient's arm or leg when it is straight, then adjustable arms 50a, 50a are adjusted so that the patient can move his or her arm or leg a predetermined number of degrees less than one hundred eighty degrees (180°) freely within the range of movement defined by the angular distance between goniometer arms 50a, 50a. Flexible stiffener 12 provides constant resistance to joint movement within the range of movement allowed as in all embodiments.

Figure 8A:
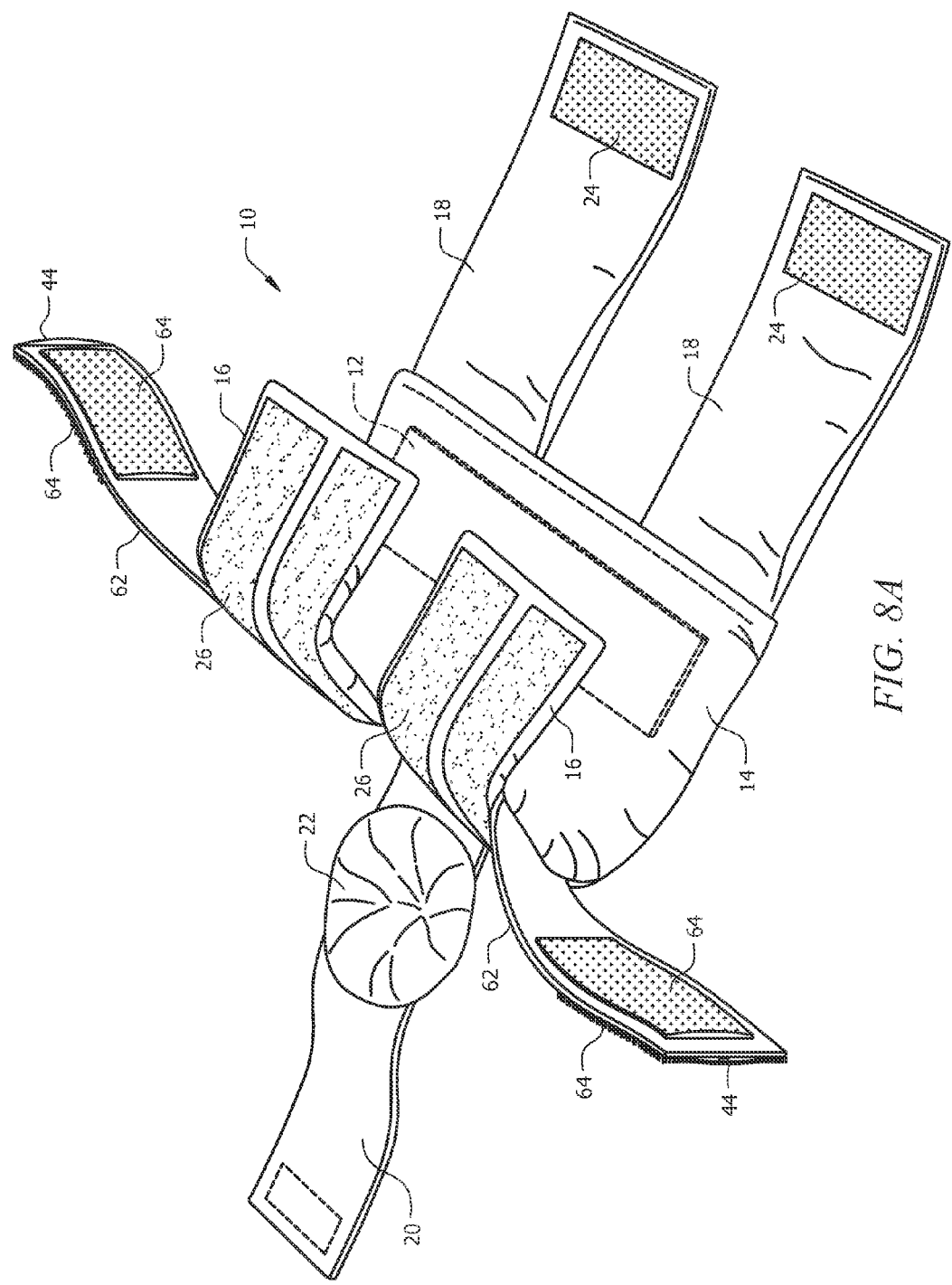
FIG. 8A is a perspective view of the elbow orthosis.
Figure 8B:
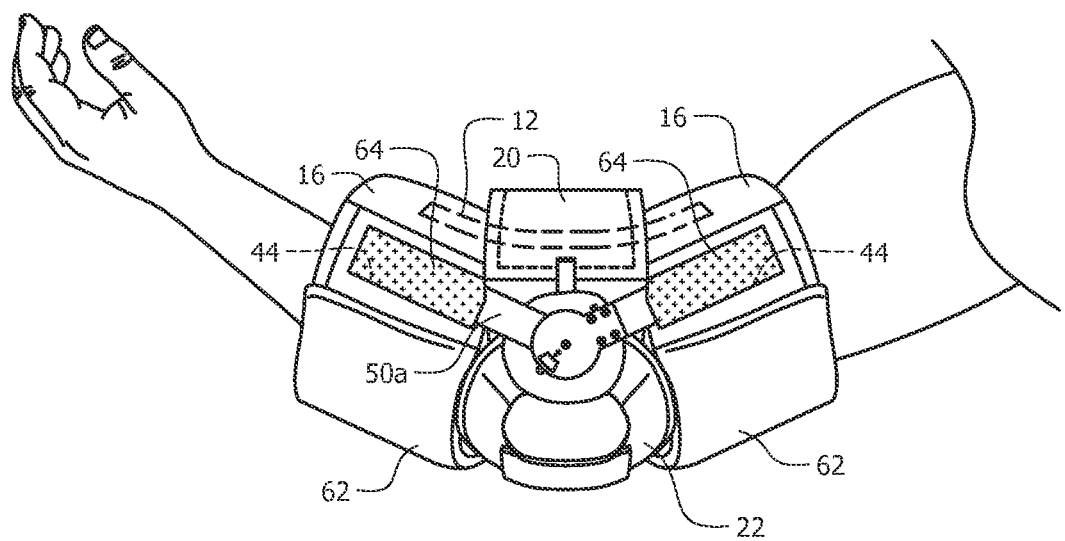
FIG. 8B is a perspective view of the elbow orthosis of FIG. 8A when in use.

FIGS. 8A and 8B depict elbow orthosis 60 when in its fully open configuration and when in use, respectively. It has a structure that is substantially similar to the structure of knee orthosis 40 but it is preferably a little smaller. Flaps 62, 62 are secured to straps 16, 16, respectively and extend therefrom in a longitudinal direction as depicted in FIG. 8A. Each side of flaps 62, 62 is covered with hook and loop fastening members 64, 64. A pocket 44 is formed in each flap 62 in the manner disclosed above.

FIG. 8B depicts rigid arms 50a, 50a of goniometer 50 positioned within said pockets. Each strap 62, 62 is folded to overlie its associated strap 16 or 18 so that each pocket 44 receives a rigid arm 50a of goniometer 50.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A method of applying an orthosis to an uncontrollably contracted joint, comprising the steps of:

providing an elongate brace having a "C" shape in transverse section, said elongate brace adapted to receive a patient's limb having an uncontrollably contracted joint;

providing a plurality of straps having respective first ends secured to said elongate brace and respective second ends releasably connected to said elongate brace so that said straps secure said patient's limb within said brace when said second ends are releasably connected to said brace;

providing an elongate pocket in said elongate brace;

positioning in said elongate pocket a dynamic flexible, elastic, flat stiffener having a uniform thickness and an inherent bias that returns said stiffener to a fat position of repose when an external force imparted to said stiffener to effect bending displacement of said stiffener from said flat position of repose is released;

bending said elongate brace and said dynamic, flexible, elastic, flat stiffener along a preselected transverse axis to momentarily overcome said inherent bias so that said elongate brace and said stiffener are bent at an angle that corresponds to an angle of contraction of said uncontrollably contract joint;

positioning said elongate brace over said uncontrollably contracted joint from a lateral direction after bending said elongate brace and said dynamic, flexible, elastic, flat stiffener along said preselected transverse axis;

releasing said elongate brace after positioning said elongate brace over said uncontrollably contracted joint from a lateral direction so that said inherent bias of said stiffener provides a constant force to said uncontrollably contracted joint to straighten said uncontrollably contracted joint;

forming said stiffener of tempered spring steel;

said tempered spring steel having spring steel having a Unified Numbering System identifier of G10950;

said tempered spring steel having a yield tensile strength between approximately 100 to 320 kilopounds per square inch;

said tempered spring steel having a modulus of elasticity of between approximately 150 to 300 GPA;

said tempered spring steel is generally planar when not flexed and having a thickness of between approximately 0.008 to 0.07 inches; and said tempered spring steel having a hardness of about 45 to 60 on the Rockwell C scale.

2. The method of claim 1, further comprising the steps of:

providing a goniometer removably mounted on said brace for allowing said patient to move said limb a predetermined number of degrees within a preselected range of movement;

providing said adjustable goniometer with a pair of rigid arms that extend radially from a central hub and which are angularly adjustable with respect to said central hub.

3. The method of claim 2, further comprising the steps of:

providing said at least one strap of said plurality of straps with two semi-rigid, malleable, and generally "C"-shaped straps;

securing a longitudinally-extending flap to each of said two semi-rigid, malleable, and generally "C"-shaped straps; and forming a pocket within each of said flaps so that each of said pockets slideably receives one of said rigid arms of said adjustable goniometer when said flaps are folded into overlying relation to their associated straps;

whereby said flaps, when tightened, create a point of contact between said uncontrolled contracted joint and said stiffener.

4. The method of claim 1, further comprising step of:
forming said stiffener of heat treated and tempered steel including between approximately 0.9 to 1.05% carbon.

* * * * *